United States Patent
Yuan et al.

(10) Patent No.: US 10,709,180 B2
(45) Date of Patent: Jul. 14, 2020

(54) PROTECTION SYSTEM AND METHOD

(71) Applicant: BOE TECHNOLOGY GROUP CO., LTD., Beijing (CN)

(72) Inventors: Zuo Yuan, Beijing (CN); Yifei Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/324,722

(22) PCT Filed: Jul. 1, 2016

(86) PCT No.: PCT/CN2016/088169
§ 371 (c)(1),
(2) Date: Jan. 8, 2017

(87) PCT Pub. No.: WO2017/117934
PCT Pub. Date: Jul. 13, 2017

(65) Prior Publication Data
US 2018/0295903 A1    Oct. 18, 2018

(30) Foreign Application Priority Data
Jan. 4, 2016 (CN) .......................... 2016 1 0006866

(51) Int. Cl.
*A41D 13/00* (2006.01)
*A41D 13/018* (2006.01)
(Continued)

(52) U.S. Cl.
CPC ........... *A41D 13/018* (2013.01); *A41D 1/002* (2013.01); *A41D 13/05* (2013.01);
(Continued)

(58) Field of Classification Search
CPC .. A41D 13/1227; A41D 31/102; B32B 5/022; B32B 5/26; B32B 27/20
See application file for complete search history.

(56) References Cited

U.S. PATENT DOCUMENTS 1,771,727 A * 7/1930 Braun ............... B64D 25/08
244/138 R
3,181,184 A * 5/1965 Potts .................. B63C 9/155
441/108
(Continued)

FOREIGN PATENT DOCUMENTS

CN   104366752 A   2/2015
CN   204908025 U   12/2015
(Continued)

OTHER PUBLICATIONS

International Search Report and Written Opinion dated Sep. 13, 2016 in PCT/CN2016/088169.
(Continued)

*Primary Examiner* — Richale L Quinn
(74) *Attorney, Agent, or Firm* — Syncoda LLC; Feng Ma

(57) ABSTRACT

This disclosure provides a protective gear and system for cushioning an object against falling. The protective gear includes a housing conforming to a portion of the object, an airbag disposed in the housing, a detector configured to detect a motion of the object; and a controller configured to generate an actuating signal to deploy the airbag if the motion is over a threshold. The protection system includes a primary protective gear and at least one secondary protective gear.

18 Claims, 4 Drawing Sheets

(51) Int. Cl.
*A41D 1/00* (2018.01)
*A61B 5/11* (2006.01)
*A41D 13/05* (2006.01)
*A41D 13/06* (2006.01)
*A41D 13/08* (2006.01)

(52) U.S. Cl.
CPC ...... *A41D 13/0512* (2013.01); *A41D 13/0525* (2013.01); *A41D 13/065* (2013.01); *A41D 13/08* (2013.01); *A41D 2400/44* (2013.01); *A61B 5/1117* (2013.01)

(56) References Cited

U.S. PATENT DOCUMENTS

| | | | | |
|---|---|---|---|---|
| 3,930,667 A * | 1/1976 | Osuchowski | A41D 13/018 | 280/730.1 |
| 4,089,065 A * | 5/1978 | McGee | A41D 13/018 | 2/2.14 |
| 4,825,469 A * | 5/1989 | Kincheloe | A41D 13/018 | 2/16 |
| 4,984,821 A * | 1/1991 | Kim | A41D 13/018 | 2/455 |
| 5,362,098 A * | 11/1994 | Guill | A41D 13/018 | 2/456 |
| 5,500,952 A * | 3/1996 | Keyes | A41D 13/018 | 2/465 |
| 5,535,446 A * | 7/1996 | Pusic | A41D 13/018 | 2/456 |
| 5,572,737 A * | 11/1996 | Valice | A41D 1/067 | 2/22 |
| 5,781,936 A * | 7/1998 | Alaloof | A41D 13/018 | 2/456 |
| 5,937,443 A * | 8/1999 | Kageyama | A41D 13/018 | 2/455 |
| 6,125,478 A * | 10/2000 | Alaloof | A41D 13/018 | 2/456 |
| 6,230,333 B1 * | 5/2001 | Umeda | A41D 13/0125 | 2/463 |
| 6,270,386 B1 * | 8/2001 | Visocekas | A41D 13/018 | 441/104 |
| 6,433,691 B1 * | 8/2002 | Hilliard | A41D 13/018 | 280/728.1 |
| 6,543,054 B2 * | 4/2003 | Gabriel | A41D 11/00 | 2/1 |
| 6,546,561 B2 * | 4/2003 | Duhamell | A41D 13/018 | 2/102 |
| 6,828,697 B2 | 12/2004 | Mattes | | |
| 6,859,939 B1 * | 3/2005 | Osburn, Sr. | A41D 13/018 | 128/869 |
| 6,859,948 B2 * | 3/2005 | Melts | A41D 13/015 | 2/465 |
| 6,920,647 B2 * | 7/2005 | Ulert | A41D 13/018 | 2/465 |
| 7,017,195 B2 * | 3/2006 | Buckman | A41D 13/018 | 2/455 |
| 7,343,632 B2 * | 3/2008 | Neron | A41D 13/018 | 2/456 |
| 7,921,472 B2 * | 4/2011 | Mazzarolo | A41D 13/018 | 2/108 |
| 8,365,316 B2 * | 2/2013 | Jan | A41D 13/018 | 2/102 |
| 8,460,354 B2 * | 6/2013 | Anderson | A61F 7/0097 | 607/108 |
| 9,107,615 B2 * | 8/2015 | Buckman | A61B 5/1117 | |
| 9,126,065 B2 * | 9/2015 | Uchida | A41D 13/018 | |
| 9,332,794 B2 * | 5/2016 | Mazzarolo | A41D 13/0512 | |
| 9,439,460 B2 * | 9/2016 | Richards | A41D 13/018 | |
| 9,468,554 B2 * | 10/2016 | Petursson | A61F 5/30 | |
| 9,622,520 B2 * | 4/2017 | Fenyves | A41D 13/018 | |
| 9,629,399 B2 * | 4/2017 | Raanan | A41D 13/0506 | |
| 9,901,125 B2 * | 2/2018 | Insley | A41D 13/00 | |
| 9,915,527 B2 * | 3/2018 | Estevo, Jr. | G01B 21/16 | |
| 9,986,771 B2 * | 6/2018 | Longinotti-Buitoni | A61B 5/0002 | |
| 10,154,695 B2 * | 12/2018 | Jin | A61B 5/1117 | |
| 10,212,974 B1 * | 2/2019 | Joshi | A41D 13/0506 | |
| 10,238,574 B2 * | 3/2019 | Freeman | A61N 1/39044 | |
| 10,271,591 B2 * | 4/2019 | Bangera | A41D 13/018 | |
| 10,368,594 B1 * | 8/2019 | LaCroix | A41D 13/0568 | |
| 2001/0049840 A1 * | 12/2001 | Atanasio | A41D 13/018 | 2/456 |
| 2002/0057946 A1 * | 5/2002 | Beltrani | B63C 11/2245 | 405/186 |
| 2002/0078484 A1 * | 6/2002 | Ulert | A41D 13/018 | 2/22 |
| 2004/0003455 A1 * | 1/2004 | Davidson | A41D 13/018 | 2/455 |
| 2005/0067816 A1 * | 3/2005 | Buckman | A41D 13/018 | 280/730.1 |
| 2012/0131718 A1 * | 5/2012 | Uchida | A62B 99/00 | 2/69 |
| 2014/0123374 A1 | 5/2014 | Gelston et al. | | |

FOREIGN PATENT DOCUMENTS

DE 4003683 A1 8/1991
WO 2012104833 A2 8/2012

OTHER PUBLICATIONS

1st Office Action dated Jul. 21, 2016 in CN201610006866.2.
Extended European Search Report (EESR) dated Jul. 24, 2019 in EP 16816164.4.

* cited by examiner

PROTECTION SYSTEM AND METHOD

CROSS-REFERENCE TO RELATED APPLICATION

The present application claims priority to Chinese Patent Application No. 201610006866.2 filed on Jan. 4, 2016, the disclosure of which is hereby incorporated by reference in its entirety.

TECHNICAL FIELD

The present disclosure relates to a protection system and method.

BACKGROUND

Elderly people may have decreased visual acuity and reduced ability to respond to falling, and some may also suffer from diseases such as osteoporosis and muscle atrophy. As a result, they may easily fall to the ground, and often incur severe injuries.

Upon falling, protruding parts of a human body, such as knees, elbows, and other joints, are prone to injuries. Some protect gears may be worn by those more susceptible to such injuries, with a focus on protecting the protruding body parts. Such devices may include wrist bracers, knee pads, and other protective gears, inside which may include internal cushion layers with elasticity and functions to cushion the impact.

For such protective gears not to severely limit a user's mobility, the internal cushion layer is typically designed not to be thick, which results in limited cushioning, and thus insufficient protection to the user.

SUMMARY

The present disclosure provides a protective gear and system, and a method thereof, aiming to protect an object against an impact.

In an aspect, a protective gear for cushioning an object against an impact is provided. The protective gear comprises a housing conforming to a portion of the object, an airbag disposed in the housing, a detector configured to detect a motion of the object; and a controller configured to generate an actuating signal to deploy the airbag if the motion is over a threshold.

In some embodiments, the protective gear is configured to cushion a part of a human body, which can be elbow, knee, neck, or waist. In some other embodiments, the protective gear is configured to cushion an object rather than a human body, which can be a delicate device, such as a large display panel, a cell phone, a scientific device, etc. There are no limitations herein.

In some embodiments, the impact against which the protective gear is configured to cushion can be falling to the ground, and can be other types of impact that is due to the change of movement. There are no limitations herein.

The housing conforming to a portion of the object refers to the shape and configuration of the housing of the protective gear which is customized based on the shape of the portion of the object. For example, to protect the elbow of a human body, the housing of the protective gear may take a shape of a ring around the elbow, so as to provide protection to the elbow against falling on the ground. In another example, to protect a corner of a delicate device, the housing of the protective gear may take a shape such that the protective gear can cover the corner well for ideal protection. There are no limitations herein.

The detector of the protective gear can comprise an acceleration sensor, which can detect acceleration of the object for indicating the motion of the object. The controller is coupled with the acceleration sensor, and is configured to determine whether falling occurs based on data of the acceleration of the object detected by the acceleration sensor, and to generate the actuating signal to deploy the airbag if determining that falling occurs.

In some embodiments of the protective gear, the acceleration sensor detects the acceleration of the object by sensing acceleration of the object along an X-axis, a Y-axis and a Z-axis in a three-dimensional coordinate system.

The protective gear can further comprise a gas generator, wherein the gas generator is disposed in the housing, and is configured to produce gas to inflate and deploy the airbag out of the housing in response to the actuating signal generated by the controller. In some embodiments, the gas generator and the airbag are arranged in an airbag groove in the housing; and an airbag outlet is arranged on an outer surface of the housing opposite to a surface of the object to be cushioned, is spatially connected with the airbag groove, and is configured to allow the airbag to expand out of the airbag groove therethrough upon inflation and deployment by the gas generator.

The gas generator can include a tip discharge device and a gas generating agent. The tip discharge device is configured to generate an electrical spark in response to the actuating signal generated by the controller; and the gas generating agent is configured to generate gas upon contacting the electrical spark. The gas generating agent can be a non-azide gas generant or liquid $CO_2$.

In some embodiments, the gas generator can further comprise a shell, which accommodates the tip discharge device and the gas generating agent, and is configured to be permeable to gas, so that the gas generated by the reaction of the gas generating agent can get into the airbag.

The airbag can be detachably mounted in the airbag groove, and the airbag groove is provided with a retractable window, arranged on a side wall that is close to the outer surface of the housing and configured to allow replacing the airbag therethrough. In some embodiments, an air inlet of the airbag can be detachably mounted on a side wall of the airbag groove via threads. The gas generator can be disposed on the side wall of the airbag groove at a position located at the air inlet of the airbag.

In some embodiments of the protective gear, the acceleration sensor and the controller can be integrated in a circuit board, and the gas generator can be coupled with the circuit board via a wire.

For embodiments of the protective gear configured to cushion a human body against falling to the ground, the airbag can fully expand within a time period less than or equal to 200 ms, and is configured to have a length of 15-20 cm and a width of 5-10 cm after deployment. Herein the length refers to a diameter of the airbag that is typically perpendicular to the direction of the impact; and the width refers to a diameter of the airbag along the direction of the impact.

In some embodiments, the housing of the protective gear can have a ring-shaped structure, encircling the object and comprises two ends for assembly or disassembly. One end is provided with at least one connector; and another end is provided with at least one mating connector; and each of the at least one connector and each of the at least one mating connector are configured to form a detachable connection between the two ends. Examples of the connector and the mating connector that can be employed can be respectively a plug and a socket, i.e. the housing of the ring-shaped protective gear can be assembled and dissembled by a detachable plug-socket connection. Other types of the connection are also possible, and there are no limitations herein.

In another aspect, the present disclosure provides a protection system for cushioning an object against falling. The protective system can comprise a primary protective gear and at least one secondary protective gear.

The primary protective gear can include a housing conforming to a portion of the object, a first airbag disposed in the housing, a detector configured to detect a motion of the object, a controller, and a first communication module, wherein the controller is configured to generate an actuating signal to deploy the first airbag if the detected motion is over a threshold, and to send the actuating signal to the first communication module; and the first communication module is coupled with the controller and is configured to transmit the actuating signal obtained from the controller Each of the at least one secondary protective gear can comprise a second communication module and a second airbag, wherein the second communication module is configured to receive the actuating signal from the first communication module of the primary protective gear and to send the actuating signal to deploy the second airbag.

In some embodiments of the protection system, the first communication module and the second communication module function in a wireless manner, but they can also work in a wired manner.

For embodiments of a protection system configured to cushion human body, the protective gear system can comprise four protective gears, two configured to be worn on elbows and another two on knees; and one protective gear is the primary protective gear, and another three protective gears are each one of the at least one secondary protective gear.

In yet another aspect, the present disclosure provides a method for cushioning an object against an impact by means of the protective gear as described above. The method comprises the following steps:

detecting a motion of the object;
determining whether the motion is over a threshold;
deploying the airbag to cushion the object against the impact if the motion is over threshold.

In some embodiments of the method, in the step of detecting a motion of the object, the motion of the object is detected by detecting acceleration of the object along an X-axis, a Y-axis and a Z-axis of a three-dimensional coordinate system in a real-time manner.

In some embodiments, the impact happens after falling of the object to ground.

The step of determining whether the motion is over a threshold can comprise the following sub-steps:

calculating a sum of acceleration vectors along the X-axis, the Y-axis and the Z-axis;
determining if the sum of acceleration vectors along the X axis, the Y axis and the Z-axis is less than or equal to the threshold and, if so, starting timing, wherein the threshold is less than maximum of the sum of acceleration vectors along the X axis, the Y axis and the Z-axis; and
determining in a preset time period, if the sum of accelerations vectors along the X axis, the Y axis and the Z-axis is less than or equal to the threshold and, if so, determining that falling happens, wherein the preset time period is less than a time period in a complete falling process.

In some of the embodiments, the threshold is in a range of 0.6-0.9 g, and preferably 0.8 g, where g is gravitational acceleration, the preset time period is in a range of 100-300 ms, and preferably 200 ms, and step S1 is performed at a frequency of ≥20/s.

Other embodiments and implementations may become apparent in view of the following descriptions and drawings.

BRIEF DESCRIPTION OF DRAWINGS

To more clearly illustrate some of the embodiments, the following is a brief description of the drawings. The drawings in the following descriptions are only illustrative of some embodiments. For those of ordinary skill in the art, other drawings of other embodiments can become apparent based on these drawings.

DETAILED DESCRIPTION

In the following, with reference to the drawings of the embodiments disclosed herein, the technical solutions of the embodiments of the invention will be described in a clear and fully understandable way. It is noted that the described embodiments are merely a portion but not all of the embodiments of the invention. Based on the described embodiments of the invention, those ordinarily skilled in the art can obtain other embodiment(s), which come(s) within the scope sought for protection by the invention.

This disclosure provides a protective gear and a method of use thereof, for cushioning an object against an impact. The object may be a human body or a delicate device. The impact may be that generated upon falling on the ground. There is no limitation herein.

In the following, description of the protective gear and the method of use thereof primarily uses an example of a human body against falling on the ground.

Embodiment 1

Figure 1:
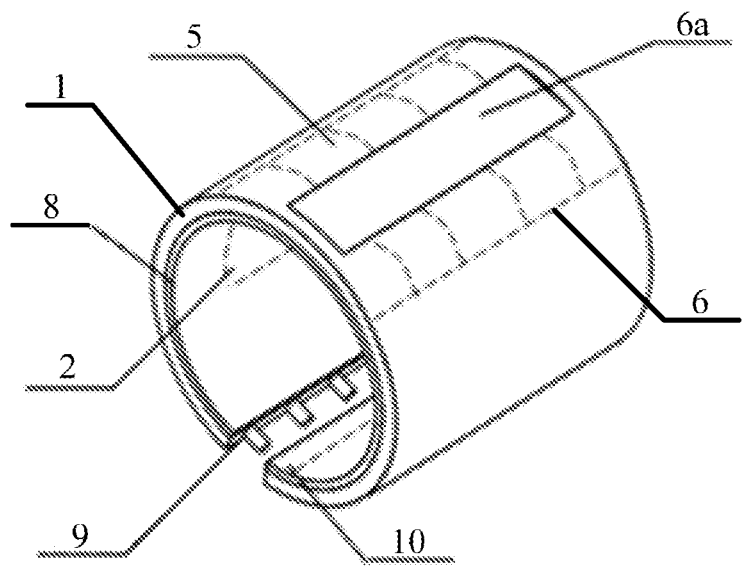
FIG. 1 is a schematic diagram of the three-dimensional structure of a protective gear according to some embodiments of the disclosure.
Figure 2:
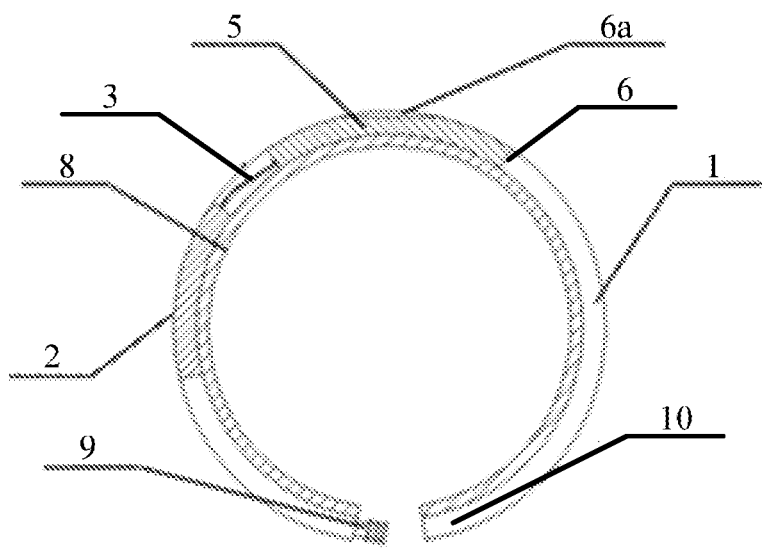
FIG. 2 is a cross-sectional view of the protective gear according to some embodiments of the disclosure.

This embodiment of the disclosure provides a protective gear, as shown in FIGS. 1 and 2. The protective gear includes a housing 1, an acceleration sensor, a controller, a gas generator, an airbag 5, and an airbag groove 6. The airbag groove 6 is arranged in the housing 1, and is provided with an airbag outlet, arranged on a side of the airbag groove 6 that is close to an outer surface of the housing 1. The gas generator and the airbag 5 are disposed in the airbag groove 6. The acceleration sensor and the controller are arranged in the housing 1. The acceleration sensor, the controller, and the gas generator are sequentially coupled. It is noted that the term "an outer surface of the housing 1" means the surface opposite to human body when the protective gear is worn on the human body, and correspondingly, the surface of the housing 1 that is close to the human body is referred an inner surface of the housing 1.

Figure 3:
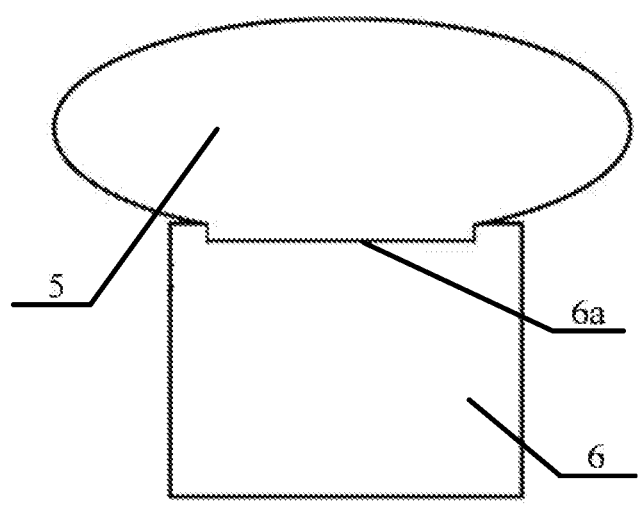
FIG. 3 is a schematic diagram of the structure of a deployed airbag provided in the protective gear.

The process in which the above protective gear protects the human body is as follows: the protective gear is worn on the body such that the airbag outlet is arranged on a side of the protective gear corresponding to a protruding part of a bent joint, in order to ensure that after ejection from the airbag groove 6, the airbag 5 is right at, and thereby capable of protecting, the protruding part of the joint while bending. The acceleration sensor detects acceleration along the X-axis, Y-axis and Z-axis of the body in a real-time manner, and the detected acceleration data are then sent to the controller. Compared with during normal walking, acceleration along the X-axis, Y-axis and Z-axis changes during falling, thus based on the acceleration data, the controller can determine whether falling occurs, and if it determines that falling happens, the controller generates an actuating signal, which is further transmitted to the gas generator. After the gas generator receives the actuating signal, it rapidly produces a large amount of gas to inflate, or pop up, the airbag 5. Rapid expansion of the airbag 5 causes the airbag to be ejected or popped out from the airbag outlet 6a. The airbag 5 that has been inflated and ejected is illustrated in FIG. 3. Because the airbag outlet is arranged on the side of the airbag groove 6 that is close to the outer surface of the housing 1, the airbag 5 is located on an outside of the housing 1 after popping up, thus can provide protection to the human body by cushioning the impact of the ground to the human body when it is about to impact the ground during falling.

It should be noted that the "X-axis, Y-axis and Z-axis" shall be referenced in a three-dimensional coordinate system during the movement of a human body. The two mutually perpendicular axes in a horizontal plane are defined as the "X axis" and the "Y-axis", and the axis perpendicular to the horizontal plane and across the intersection of the X axis and the Y axis is defined as the "Z-axis."

Because the cushioning effect of the airbag 5 is much larger than the cushion layer typically used in conventional protective gears, the protective gear disclosed herein provides protection to a falling body by arranging the airbag 5 in the protective gear.

In addition, since the airbag 5 is located in the airbag groove 6 under normal situations, and will be inflated and popped out of the airbag groove 6 only when falling occurs, so the airbag 5 occupies little space in the protective gear. The acceleration sensor, controller and gas generators are all relatively small, so these parts do not lead to an increased thickness and weight for the protective gear.

Figure 4:
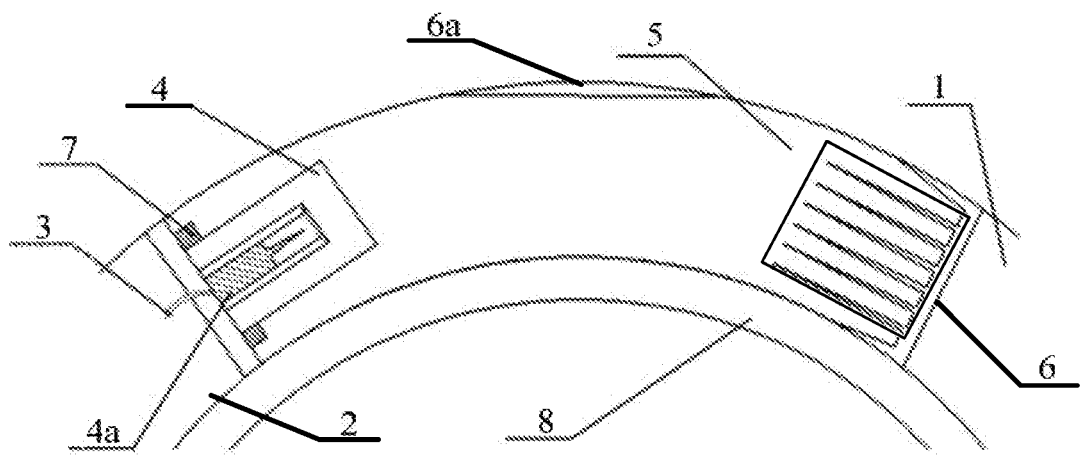
FIG. 4 is a schematic diagram of an internal structure of an airbag slot provided in the protective gear.

In the protective gear as shown in FIG. 4, a gas generator 4 may include a tip discharge device 4a and a gas generating agent. The tip discharge device 4a is coupled to the controller, and after receiving the actuating signal transmitted by the controller, the tip discharge device 4a can generate an electrical spark. The gas generating agent is a substance that under fire or heat will have a violent reaction such that a large amount of gas is quickly produced. Thus upon exposure of the electrical spark generated by the tip discharge device 4a, the gas generating agent quickly produces a large amount of gas, which goes into and inflates the airbag 5. A gas generating agent can be a non-azide gas generant or liquid $CO_2$. Furthermore, the gas generator may also include a shell 4, configured to accommodate the tip discharge device 4a and the gas generating agent. The shell is configured to be permeable to gas, so that the gas generated by the reaction of the gas generating agent can get into the airbag 5.

To facilitate maintenance and/or replacement, the airbag 5 can be detachably mounted in the airbag groove 6, and as such a retractable window can be arranged on a side wall of the airbag groove 6 that is closer to the outer surface of the housing 1. When it is required for replacement/maintenance of the airbag 5, the retractable window on the airbag groove can be opened to dismount, or detach, the airbag 5. There are multiple approaches to detachably mount the airbag 5. As shown in FIG. 4, an air inlet of the airbag 5 can be mounted on the side wall of airbag groove 6 via threads 7. On the basis of this structure, in order to facilitate the gas to go into and inflate the airbag 5, the gas generator 4 can be also installed on the side wall of the airbag groove 6 at a position located at the air inlet of the airbag 5.

If the volume of the airbag 5 is too small after full expansion, the cushioning effect is limited, and airbag 5 cannot effectively protect the human bodies. If the volume of the airbag 5 is too large after full expansion, inflation time may be too long for a complete expansion before falling on the ground, affecting the protective effects of the protective gear. Thus the volume of the airbag 5 after full expansion is preferably controlled within a reasonable range. Assuming a constant inflation speed, the volume of the airbag 5 after full expansion depends on inflation time, and in order to fully expand the airbag 5 before falling, the inflation time should be within the time period from when the human body loses balance to when the body falls to the ground. As such the time period from when the airbag starts inflation to when it is fully expanded is preferably less than or equal to 200 ms, so that the volume of the fully expanded airbag 5 is controlled within a reasonable range. In some embodiments, a fully expanded airbag 5 can have a length of 15-20 cm and a width of 5-10 cm, to ensure that the air bag 5 can have a sufficient cushioning effect. Herein the length refers to a diameter of the airbag that is typically perpendicular to the direction of the impact; and the width, or thickness, refers to a diameter of the airbag along the direction of the impact.

In order to increase the integration level of all parts inside the protective gear, and to reduce the space occupied by these parts, the acceleration sensor and the controller can be integrated on a circuit board 2 in some embodiments, as shown in FIG. 4. The circuit board 2 can be arranged on one side of the airbag groove 6. The gas generator 4 can be coupled with the circuit board 2 via a wire 3, configured to realize an electrical coupling between the gas generator 4 and the controller of the circuit board 2. In order to reduce the length of the wire 3, the circuit board 2 can be arranged at a proximity of the gas generator 4.

The protective gears provided in this embodiment may take a ring-shaped structure, which can be worn around parts, such as elbows, knees etc. of the human body. In order to achieve a wearable function of the protective gear as shown in FIGS. 1 and 2, the protective gear can be disassembled at a side opposite to the side of the airbag groove 6. Among the two ends of the dissembled protective gear, one end can provided with plugs 9, and the other end can be provided with sockets 10 which correspondingly matches with the plugs 9, and by snap-fit or securely connection, of the plugs 9 with the sockets 10, the protective gear can be worn on the human body. Other means may be arranged on the protective gear to play a similar role to allow the wearing of the protective gear on the human body.

In order to further improve the protective effect of the protective gear, a cushion layer 8 may be arranged at an inside surface of the housing 1, as shown in FIGS. 1, 2 and 4. The cushion layer 8 can be made of an elastic material such as sponge. When a human body falls, the cushion layer 8 can have elastic deformation to cushion the impact of the ground to the body, to thereby play a protective role.

In some embodiments, the housing 1 of the protective gear can be made of a material such as a hard plastic or a metal, which is configured to prevent friction between the body and the ground when falling occurs.

The protective gear as described above can be used to protect elbows, knees and other parts of the body. Take a protective gear for elbow as an example. When wearing the protective gear, the airbag outlet shall be arranged to be on a side corresponding to the protruding part of a bent elbow, to ensure that the airbag 5 ejected and popped up from the airbag outlet 6a can be located on the protruding side of the bent elbow. This configuration ensures that when a body is about to impact the ground after falling, the airbag is right on the protruding side of a bent elbow, which can cushion the impact of the ground to the protrusion part of the elbow. A knee protective gear is worn and works in a similar manner.

Embodiment 2

On the basis of Embodiment 1, Embodiment 2 provides a protective gear system, which comprises a primary protective gear, at least one secondary protective gear, and at least one wireless communication module. The primary protective gear can be the protective gear as described above in Embodiment 1. Compared with the protective gear as described in Embodiment 1, a secondary protective gear lacks an acceleration sensor and a controller, and includes a housing, an airbag groove, a gas generator and an airbag, whose specifications can be referenced by the housing 1, the airbag groove 6, the gas generator 4 and the airbag 5, as disclosed in Embodiment 1. Both the primary protective gear and each of the at least one secondary protective gear are provided with a wireless communication module; the wireless communication module of the primary protective gear is coupled to a controller of the primary protective gear, whereas the wireless communication module of the secondary protective gear is coupled to the gas generator in the secondary protective gear.

The acceleration sensor of the primary protective gear detects acceleration of human body along the X-axis, Y-axis and Z-axis in a real-time manner. When falling occurs, based on the acceleration data of the human body along the X-axis, Y-axis and Z-axis detected by the acceleration sensor, the controller of the primary protective gear determines whether falling occurs, and if it determines that falling happens, the controller generates an actuating signal, and further sends the actuating signal to the gas generator 4. The gas generator rapidly produces a large amount of gas to inflate and expand the airbag 5. At the same time, via the wireless communication module of the primary protective gear, the actuating signal is transmitted to the wireless communication module of the secondary protective gear, which further sends an actuating signal to the gas generator 4 arranged in the secondary protective gear, so that the air bag 5 is inflated and expanded, to thereby play protective roles of the primary protective gear and the secondary protective gear.

In the protective gear system described above, airbags 5 are configured to play a cushioning function to a human body against the impact of the ground when falling occurs. Since airbags 5 have a larger cushioning effect than the cushion layer commonly used in current protective gears, the protective gear system has an improved protection.

Additionally in this embodiment, only one set of acceleration sensor and controller is arranged on one, but not the rest, of a plurality of protective gears in the protective gear system, and the plurality of protective gears are able to communicate with one another through the wireless communication modules. By this configuration, one protective gear can simultaneously control the airbags 5 in multiple protective gears to expand, without the need to arrange acceleration sensors and controllers in each of the plurality of protective gears, thereby leading to a saving on the number of acceleration sensors and controllers. Thus the cost of the protective gear system is reduced and its structure is simplified.

Figure 5:
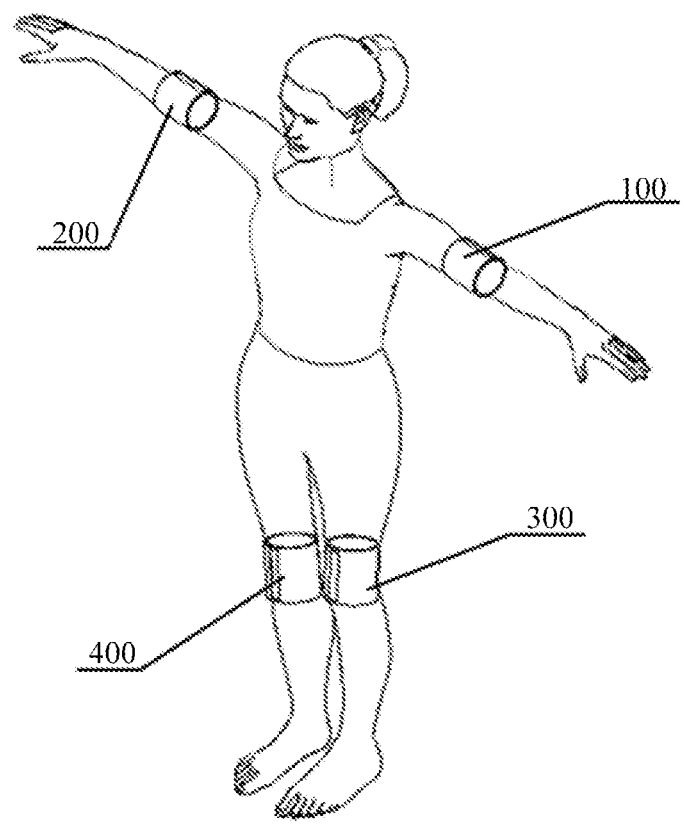
FIG. 5 is a structural diagram of a protective gear system according to some embodiments of the disclosure.

In some embodiments, the protective gear system may include two protective gears for elbows (or elbow protective gears) and two protective gears for knees (or knee protective gears). Any one of the four protective gears can be the primary protective gear and the remaining three the secondary protective gears. In one embodiment as shown in FIG. 5, the protective gear system includes a primary elbow protective gear 100, a secondary elbow protective gear 200, a secondary knee protective gear 300, and a secondary knee protective gear 400. Each of the protective gears is provided with a wireless communication module. When the primary elbow protective gear 100 detects that falling occurs, its controller controls its airbag 5 to expand, and transmits an actuating signal to the secondary elbow protective gear 200, the secondary knee protective gear 300 and the secondary knee protective gear 400, respectively, to expand their respective airbags 5.

It should be noted that, for the above-mentioned protective gear system, in order to ensure the airbags 5 to be able to cushion the body when falling, the airbag outlets 6a are preferably arranged on a side corresponding to the protruding side of human joints during wearing of the protective gear system. Specifically for the primary elbow protective gear 100 and the secondary elbow protective gear 200, because the elbow joints protrude toward the rear side of the body when they are bent, when wearing they should be configured such that their airbag outlets are arranged to point to the rear side of the body. For the secondary knee protective gear 300 and the secondary knee protective gear 400, because the knee joints protrude toward the front of the body when they are bent, when wearing they should be configured such that their airbag outlets are arranged to point to the front of the body.

The protective gear system as described in this embodiment can also include protective gears for other parts of the body, such as head, neck, waist, etc., so as to provide more comprehensive protection to a human body when falling.

Embodiment 3

Figure 6:
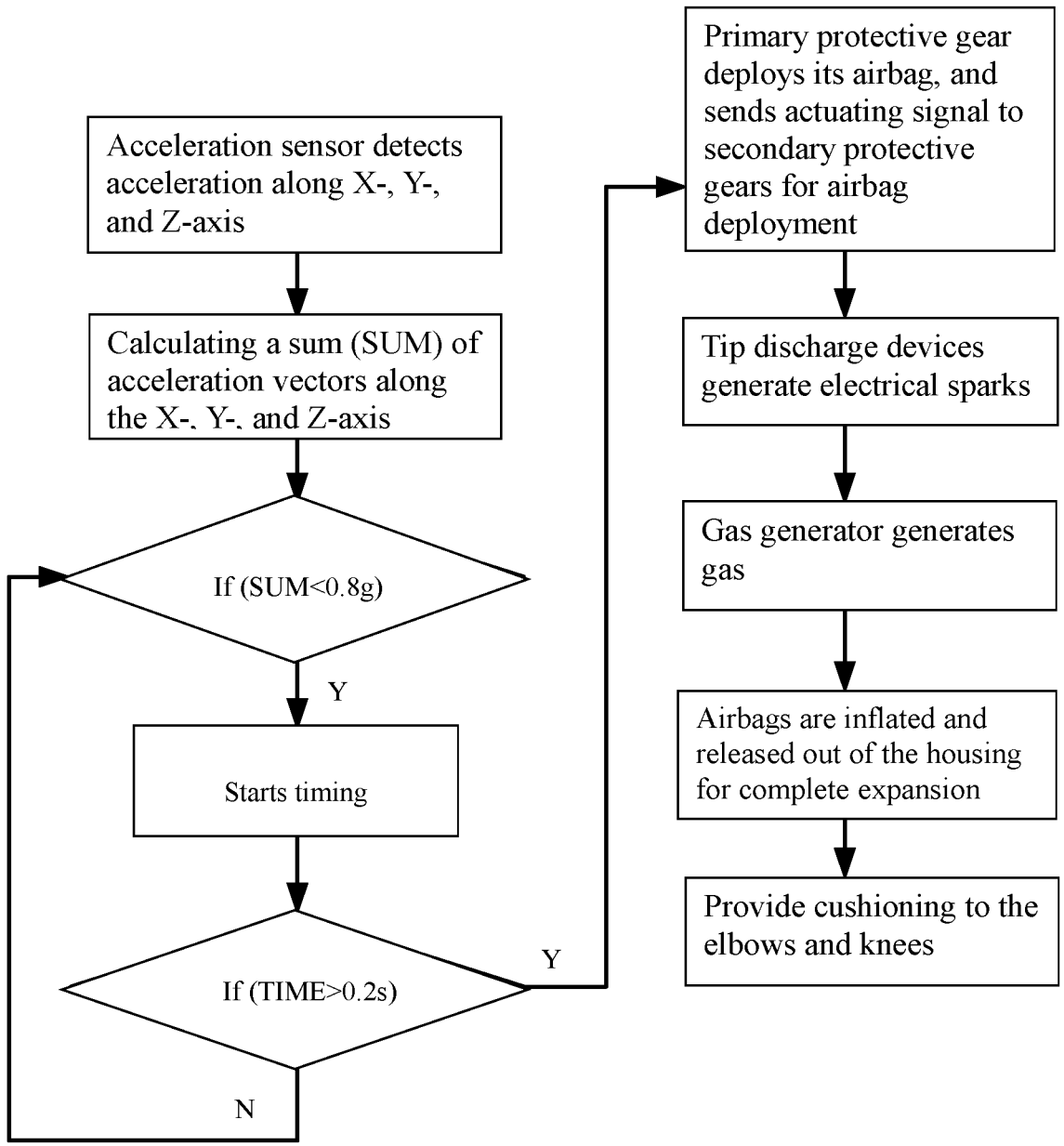
FIG. 6 is a flowchart of a method for fall protection according to some embodiments of the disclosure.

In this embodiment, a method for fall protection is provided. The method for fall protection can be applied to a protective gear as described in Embodiment 1, and a protective gear system as described in Embodiment 2. As shown in FIG. 6, the method for fall protection comprises:

Step S1: detecting acceleration of a human body along the X-axis, Y-axis and Z-axis in a real-time manner;

Step S2: determining whether falling occurs, and proceeding to step S3 if determining that falling occurs;

Step S3: controlling the gas generator 4 to generate gas, wherein the gas inflates the airbag 5 to allow the airbag 5 to be ejected from the airbag outlet 6a.

This embodiment utilizes airbags 5 to provide protection when a human body falls. Additionally, the method for fall protection as described above can detect acceleration of the human body along the X-axis, Y-axis and Z-axis in a real-time manner, and can determine whether falling occurs. When falling happens, the airbag 5 is inflated and expanded automatically, which can cushion the impact of the ground to the human body, thereby realizing an intelligent and automatic fall protection.

In some embodiments of the method for fall protection as described above, also as shown in FIG. 6, step S2 may include the following steps:

Step S21: calculating a sum of the acceleration vectors along the X-axis, Y-axis and Z-axis of a human body;

Step S22: determining if the sum of the acceleration vectors along the X-axis, Y-axis and Z-axis of the human body is less than or equal to a threshold value of the sum of the acceleration vectors, and if yes, starting timing and proceeding to step S23;

Step S23: determining within a continuous preset time period, if the sum of the acceleration vectors along the X-axis, Y-axis and Z-axis of the human body is less than or equal to the threshold value of the sum of the acceleration vectors, and if yes, determining that fall happens.

It should be noted that the "threshold value of the sum of the acceleration vectors" should be less than the maximum value for the sum of acceleration vectors along the X-axis, Y-axis and Z-axis of the human body, to ensure an accuracy in determining if falling occurs. After actual calculation, when falling happens accidentally, the sum of the acceleration vector along the X-axis, Y-axis, and Z-axis of a human body is typically less than 1 g (g is the gravitational acceleration, having a value of 9.8 m/s2), and thus the threshold value of the sum of the acceleration vectors should be set to be smaller than 1 g.

In addition, the "preset time period" should be less than the whole time period of falling, so as to ensure an accuracy in determining if falling occurs. When falling occurs, the human body instantly loses balance, and the whole falling process is essentially the process in which the body's gravity center falls down from a certain height to the ground. The whole time period of falling is set as t, the reduced height of the body's gravity center is set as h, and based on $$h = \frac{1}{2}gt^2,$$

and a given h, the whole time period of falling t can be calculated. Assuming h=1 m, t can be 452 ms, and as such the "preset time period" should be set to be less than 452 ms.

In the whole falling process, the sum of acceleration vectors along the X-axis, Y-axis and Z-axis gradually reduces to zero, thus when the sum of acceleration vectors is initially detected to be less than the threshold value of the sum of the acceleration vectors, it indicates that falling may likely occur, and timing starts from here, and the acceleration along the X-axis, the Y-axis and the Z-axis is continuously detected. If the sum of acceleration vectors along the X-axis, the Y-axis and the Z-axis becomes less than the threshold value of the sum of the acceleration vectors within the preset time period, the probability of falling becomes very high, it can be determined that falling occurs.

To improve the judging accuracy and prevent automatic pop-up and expansion of airbags 5 under false judgement, a large number of tests have been performed to optimize the threshold value for the sum of acceleration vectors, and it is observed that a threshold value in a range of 0.6-0.9 g corresponds to a relatively high judging accuracy, and more specifically of 0.8 g to the highest.

To improve the judging accuracy and allow sufficient time for timely inflation and complete expansion of airbags 5, a large number of tests have been performed to optimize the preset time period, and it is observed that a preset time period in a range of 100-300 ms corresponds to a relatively high judging accuracy, and more specifically of 200 ms to the highest.

Regardless of normal walking or falling, detection of acceleration along the X-axis, Y-axis and Z-axis by the acceleration sensor is performed in a real-time manner. The more frequently the acceleration sensor detects, the more the judgement to determine if the sum of acceleration vector along the X-axis, Y-axis and Z-axis of a human body is less than or equal to the threshold value within the preset time period, and the higher the judging accuracy. In the above embodiments, the detection frequency of the acceleration sensor can be greater than or equal to 20/s, i.e., for a preset time period of 200 ms, the acceleration sensor needs to detect at least 4 times to guarantee a high judging accuracy in determining whether falling happens.

It should be noted that, the protective gear requires to be worn such that the airbag outlets are arranged on a side of the protective gears corresponding to the protruding part of the body joints in order for the airbags 5 to sufficiently cushion the impact of the ground to the body upon falling. This configuration ensures that after ejection from the airbag outlets, the airbags 5 is right beneath the protrusion parts of the bent joints.

Although specific embodiments have been described above in detail, the description is merely for purposes of illustration. It should be appreciated, therefore, that many aspects described above are not intended as required or essential elements unless explicitly stated otherwise. Various modifications of, and equivalent acts corresponding to, the disclosed aspects of the exemplary embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. A protective gear for cushioning a subject against an impact, comprising:
    a housing conforming to a body joint of the subject;
    an airbag disposed in the housing;
    a detector comprised of an acceleration sensor, configured to detect an acceleration subject for indicating a motion of the subject; and
    a controller coupled with the acceleration detector, configured to determine whether falling occurs based on data of the acceleration of the subjection detected by the acceleration sensor, and to generate an actuating signal to deploy the airbag if the motion is over a threshold,
wherein the acceleration sensor detects the acceleration of the subject by sensing acceleration of the object along an X-axis, a Y-axis, and a Z-axis in a three-dimensional coordinate system, the threshold is determined by a sum of the acceleration vectors along the X, Y, Z axis and the vector sum is less than 1g.

2. The protective gear according to claim 1, wherein the protective gear is configured to cushion a human body or a delicate device.

3. The protective gear according to claim 1, wherein the impact happens after falling of the object to ground.

4. The protective gear according to claim 1, further comprising a gas generator, wherein the gas generator is disposed in the housing, and is configured to produce gas to inflate and deploy the airbag out of the housing in response to the actuating signal generated by the controller.

5. The protective gear according to claim 4, wherein:
the gas generator and the airbag are arranged in an airbag groove in the housing; and
an airbag outlet is arranged on an outer surface of the housing opposite to a surface of the joint to be cushioned, is spatially connected with the airbag groove, and is configured to allow the airbag to expand out of the airbag groove therethrough upon inflation and deployment by the gas generator.

6. The protective gear according to claim 4, wherein the gas generator comprises a tip discharge device and a gas generating agent, wherein:
the tip discharge device is configured to generate an electrical spark in response to the actuating signal generated by the controller; and
the gas generating agent is configured to generate gas upon contacting the electrical spark.

7. The protective gear according to claim 6, wherein the gas generating agent is selected from a non-azide gas generant or liquid $CO_2$.

8. The protective gear according to claim 5, wherein the airbag is detachably mounted in the airbag groove, and the airbag groove is provided with a retractable window, arranged on a side wall that is close to the outer surface of the housing and configured to allow replacing the airbag therethrough.

9. The protective gear according to claim 1, wherein the acceleration sensor and the controller are integrated in a circuit board.

10. The protective gear according to claim 2, wherein the protective gear is configured to cushion a joint selected from one of elbow, knee, neck, or waist, and the impact happens after falling of the part of the body joint to ground.

11. The protective gear according to claim 1, wherein the housing has a ring-shaped structure, encircling the body joint of the subject and comprises two ends for assembly or disassembly, wherein:
one end is provided with at least one connector;
another end is provided with at least one mating connector; and
each of the at least one connector and each of the at least one mating connector are configured to form a detachable connection between the two ends.

12. The protective gear according to claim 11, wherein the at least one connector and the at least one mating connector are respectively a plug and a socket, or a socket and a plug.

13. A protection system for cushioning an object against falling, comprising a primary protective gear according to claim 1, and at least one secondary protective gear, wherein:
each of the at least one secondary protective gear comprises a second communication module and a second airbag, wherein the second communication module is configured to receive the actuating signal from the first communication module of the primary protective gear and to send the actuating signal to deploy the second airbag.

14. The protection system according to claim 13, wherein the first communication module and the second communication module function in a wireless manner.

15. The protection system according to claim 14, wherein the object is a human body, the protective gear system comprises four protective gears, two configured to be worn on elbows and another two on knees; and one protective gear is the primary protective gear, and another three protective gears are each one of the at least one secondary protective gear.

16. A method for cushioning an object against an impact with the protective gear according to claim 1, the method comprising:
detecting a motion of the object;
determining whether the motion is over a threshold; deploying the airbag to cushion the object against the impact if the motion is over the threshold.

17. The method according to claim 16, wherein the motion of the object is detected by detecting acceleration of the object along an X-axis, a Y-axis and a Z-axis of a three-dimensional coordinate system in a real-time manner.

18. The method according to claim 17, wherein determining whether the motion is over a threshold comprising:
calculating a sum of acceleration vectors along the X-axis, the Y-axis and the Z-axis;
determining if the sum of acceleration vectors along the X axis, the Y axis and the Z-axis is less than or equal to the threshold and, if so, starting timing, wherein the threshold is less than maximum of the sum of acceleration vectors along the X axis, the Y axis and the Z-axis; and
determining in a preset time period, if the sum of accelerations vectors along the X axis, the Y axis and the Z-axis is less than or equal to the threshold and, if so, determining that falling happens, wherein the preset time period is less than a time period in a complete falling process.

* * * * *